United States Patent [19]

Terstappen et al.

[11] Patent Number: 5,622,853
[45] Date of Patent: Apr. 22, 1997

[54] T LYMPHOCYTE PRECURSOR

[75] Inventors: Leon W. M. M. Terstappen, Palo Alto, Calif.; Louis J. Picker, Dallas, Tex.

[73] Assignee: Becton Dickinson and Company, Franklin Lakes, N.J.

[21] Appl. No.: 669,142

[22] Filed: Mar. 14, 1991

Related U.S. Application Data

[63] Continuation-in-part of Ser. No. 517,101, May 1, 1990, abandoned.

[51] Int. Cl.$^6$ .............. C12N 5/00; G01N 33/53; F01N 1/02
[52] U.S. Cl. .............. 435/372.3; 435/7.2; 435/2; 435/325
[58] Field of Search .............. 435/172.3, 240.2, 435/240.21, 2

[56] References Cited

U.S. PATENT DOCUMENTS

| | | | |
|---|---|---|---|
| 4,624,925 | 11/1986 | Kung et al. | 435/68 |
| 4,680,383 | 7/1987 | Kung et al. | 530/387 |
| 4,714,680 | 12/1987 | Civin | 435/240.25 |
| 4,798,806 | 1/1989 | Kung et al. | 436/548 |
| 4,803,262 | 2/1989 | Kung et al. | 530/387 |
| 4,845,653 | 7/1989 | Conrad | 364/521 |
| 4,987,086 | 1/1991 | Brosnan | 436/501 |
| 5,047,321 | 9/1991 | Loken et al. | 435/6 |

OTHER PUBLICATIONS

Civin et al., Int'l J. Cell Cloning, 5;267 (1987).
Loken et al. Blood, 70:1316 (1987).
Loken et al., Blood 69:255 (1987).
Terstappen et al Leukemia, 4:657 (1990).
Terstappen et al. J. Anal. Cell Pathol. 2:229 (1990).
Sci. Amer. Medicino, vol. 2, Ch. 6 § I (1990).
Leukocyte Typing IV, App. A Oxford Univ. Press.
Terstappen et al., Blood 77, 1218 (Mar. 15, 1991).
Terstappen et al., Blood 76 1739 (1990).

*Primary Examiner*—Suzanne E. Ziska
*Attorney, Agent, or Firm*—Robert M. Hallenbeck; Royal N. Ronning, Jr.

[57] ABSTRACT

A population of T lymphocyte precursor cells is disclosed. In bone marrow, the earliest identifiable T lymphocyte precursor is $CD34^+$, $CD7^+$ and Leu $8^{+++}$. Methods of isolation and methods of therapeutic use of such cells also are disclosed.

1 Claim, 20 Drawing Sheets

5,622,853

T LYMPHOCYTE PRECURSOR

This application is a continuation-in-part of an earlier filed application Ser. No. 517,101, filed May 1,1990, now abandoned.

FIELD OF THE INVENTION

This invention relates to a population of cells comprising the T lymphocyte precursor, and more particularly relates to methods of isolation and identification of such cells in biological samples. The invention further relates to methods of using populations of such cells to treat hematologic and immunologic disorders.

BACKGROUND OF THE INVENTION

Hematopoiesis is the biological mechanism by which the cells of the hematopoietic system develop and differentiate. Hematopoiesis is believed to originate with hematopoietic stem cells in the yolk sac. This pluripotent stem cell then seeds to the liver at a gestational age of approximately 8 weeks. The liver is the first organ in which hematopoietic cells differentiate to produce cells of various lineages.

At approximately 12 weeks of gestational age, the stem cells also seed the other hematopoietic organs (i.e., spleen, bone marrow, thymus and lymphatic tissues). The bone marrow then takes over the role of the liver gradually, and by approximately 24 weeks, the bone marrow has taken over fully. Although the liver and spleen are believed to maintain some number of pluripotent stem cells, they usually only play a role in hematopoiesis beyond the gestational stage when there is a severe reduction in the content of the bone marrow. U.S. Ser. No. 517,101 describes a population of stem cells that comprise the pluripotent hematopoietic stem cell. This population can be identified on the basis of expression of certain cell surface antigens. Specifically, this population is $CD34^+/CD38^-$. CD34 is the surface antigen common to all stem cells. See U.S. Pat. Nos. 4,965,204 and 4,714,680.

When fully developed, the human hematopoietic system is populated by cells of several different lineages. These differentiated cells may appear in bone marrow, thymus, spleen, liver, lymphatic tissue(s) and in peripheral blood. Within any specific lineage, there are a number of maturational stages. In most instances, the more immature developmental stages occur within bone marrow while the more mature and final stages of development occur in peripheral blood.

There are three major lineages: the erythroid lineage which matures into red blood cells; the myelomonocytic lineage which matures into granulocytes (including neutrophils, eosinophils and basophils) and monocytes; and the lymphoid lineage which matures into B lymphocytes, T lymphocytes and NK cells. (The megakaryocytes may be considered a fourth lineage which gives rise to platelets.) Within each lineage and between each lineage, antigens are expressed differentially on the surface and in the cytoplasm of the cells in a lineage. The expression of one or more antigens and/or the intensity of expression are used to distinguish between maturational stages within a lineage and between lineages. Loken and Terstappen have published a series of papers which describe the maturational development of B lymphocytes (Blood, 70:1316, (1987)), the development of erythroid cells (Blood, 69:255, (1987)), the development of neutrophils (Leukemia, 4:657 (1990) and mono-myeloid cells (J. Anal. Cellular Pathol., 2:229 (1990)). In each of these cases, Loken and Terstappen worked backward from the most mature stage in peripheral blood and described the changes in light scattering and antigen expression on less differentiated cells. Distinct maturational stages could be assigned to differentiating populations of cells. Thus, for example, using B lymphocytes, Loken et al. defined four stages of development: "stage B IV" comprised the mature B lymphocytes, "stage B III" represented the immature B cell, "stage B II" represented a more immature pre-B cell and "stage B I" represented the earliest B lymphoid cell. Similar stages of development are described for each of the other lineages.

As noted in FIG. 8 of the first paper, Loken et al. defined antigen expression for each of the four described stages. Stage B I was defined by the relatively high expression of both CD34 and CD10. In stage B II, expression of CD34 decreased to very low levels, CD10 expression decreased slightly and levels of CD19, HLA-DP and HLA-DR increased significantly. In stages B III and B IV, expression of CD20, CD22 and CD21 also significantly increased.

B lymphocytes are an important part of the hematopoietic system in that these cells produce antibodies that form a major component of the immune system. T lymphocytes, on the other hand, have a number of functions which form another major component of the immune system. T lymphocytes help B lymphocytes make antibodies, recognize and destroy cells infected with viruses, activate phagocytes to destroy pathogens and control the level and quality of the immune response. The ability of both T and B lymphocytes to recognize the enormous variety of antigens to which they may be exposed results from recombination and gene rearrangement of the antigen receptor genes during development.

T lymphocytes, unlike B lymphocytes (and cells of most other lineages), develop and mature in the thymus. During embryonic development, the thymus is believed to be seeded by the T lymphocyte precursor cells first from the liver and then from the bone marrow. These precursor cells are believed to differentiate from a common lymphoid precursor, as yet undefined. From this common lympholld precursor, the precursors to B lymphocytes, NK cells and T lymphocytes develop.

The T lymphocyte precursors that seed the thymus are believed to be immuno-incompetent (i.e., they are unable to respond to specific antigens presented in association with MHC class II antigens and are unable to distinguish between self and foreign antigens.) Once in the thymus, the T lymphocyte precursors are believed to undergo three stages of differentiation as they transit from the cortex to the medulla and finally into the peripheral blood. During the period the cells reside in the thymus, the cells are referred to as thymocytes. Differentiation of thymocytes to mature lymphocytes is measured by the expression of certain cell surface antigens. The following antigens are expressed on thymocytes and T lymphocytes.

CD1 is an antigen of approximately 45 kD and is found on approximately three-fourths of cortical thymocytes. CD1 is involved in antigen presentation.

CD2 is antigen of approximately 50 kD that is expressed on nearly all T lymphocytes and thymocytes and on a subset of NK cells. CD2 is the E rosette receptor.

CD3 is an antigen of approximately 25–28 kD that is found on all mature T lymphocytes and on approximately three-fourths of thymocytes. CD3 has several chains and normally is found complexed with the T cell receptor. (TCR is a dimer composed of α and β or γ and δ subunits).

CD4 is an antigen of approximately 55 kD that is expressed on a major subset of mature T lymphocytes and nearly all thymocytes. This subset functions to help B lymphocytes to produce antibodies against a specific antigen.

CD5 is an antigen of approximately 67 kD and is found T lymphocytes, a distinct subset of B lymphocytes and thymocytes.

CD7 is an antigen of approximately 40 kD and is found on T lymphocytes, thymocytes and NK cells.

CD8 is an antigen complex consisting of two disulfide bonded subunits of approximately 32 and 43 kD. It is found on a major subset of mature T lymphocytes and the majority of thymocytes. This subset functions in the destruction of allogenic cells and virally infected target cells.

Leu 8 is an antigen of approximately 70–80 kD and is present on approximately three-fourths of T lymphocytes, approximately 45% of thymocytes, a subset of NK cells and most B cells. Leu 8 is involved in the homing of lymphocytes to peripheral lymph nodes and is also known as LECAM-1.

For a more detailed description of thymocytes and mature T lymphocytes, subsets thereof and their development and relationship to B lymphocytes, see Sci. Amer. Medicine, vol. 2, ch. 6, §I, Rubenstein and Federman eds. (1990), and see Leukocyte Typing IV, App. A, Oxford Univ. Press, Knapp et al. eds. (1989).

Because of the role of the T lymphocyte in the immune response, the loss or impairment of T cell function is important. Briefly, function can be lost or impaired as a result of a hereditary condition, damage to the thymus, drug treatment or other therapies and disease. These conditions are associated with a marked impairment of cell-mediated immune functions such as the ability to respond to infection. In addition, there can be an impairment of ability to fight tumors and to participate in and direct antibody mediated responses.

Hereditary conditions included PNP-deficiency, Di George's syndrome and chronic mutocutane candidasis. Disease conditions include viral infection (e.g., HIV infection which results in a destruction of $CD4^+$ T lymphocytes), autoimmune disease (e.g., juvenile diabetes and systemic lupus erythromatous which result in a loss of regulation of auto-antibodies) and leukemias (e.g., T-CLL and T-ALL). Drug and other treatments include immunosuppressive drugs (e.g., cyclosporine), chemotherapy and total body irradiation.

In each of these instances, repopulation, regeneration or replacement of one or more mature T lymphocyte subsets may be desired. For example, in HIV infections, repopulation of the $CD4^+$ T lymphocyte subset is desirable. In autoimmune disease, replacement of only the T lymphocytes that attack self with properly functioning T lymphocytes is desirable. In those patients who have received immunotherapy, the addition of competent T lymphocytes is desirable to prevent relapse or opportunistic infection. In still other patients with T lymphocyte leukemias (e.g., T-ALL and T-CLL), removal of the leukemic cells followed by replacement with new T lymphocytes is desirable.

Because of the immunocompetence of mature T lymphocytes, one cannot use such mature cells from one person to repopulate or replace the T lymphocytes of another person having one of the above-mentioned conditions. Accordingly, if one is repopulate or replace the defective or impaired T lymphocytes, one must begin with immuno-incompetent cells. Further, it is more desirable to begin with the T lymphocyte precursor, as opposed to a stem cell, in order to generate only T lymphocytes and to it as rapidly as possible.

Accordingly, what is desired is a method to isolate and identify a population of T lymphocyte precursor cells. Once isolated, transplantation or transfusion of genetically altered or unaltered precursor cells can be effected.

SUMMARY OF THE INVENTION

One aspect of this invention comprises the isolation and identification of a substantially pure population of T lymphocyte precursor cells. "Substantially pure", as used herein, is defined as greater than or equal to 90% purity as measured by multiparameter fluorescence activated cell sorting of the type described hereinafter. This population can be subdivided into two subsets: those T lymphocyte precursor cells which are present in both bone marrow and thymus; and those cells found only in the bone marrow. The earliest of the precursors comprise those cells found only in bone marrow. Both subsets, however, further comprise immuno-incompetent cells. Depending upon the therapy and disease to be treated either or both of these populations can be used. Unless specifically mentioned, the term "T lymphocyte precursor" will include either or both subsets.

In a one embodiment of this invention, a population of the earliest T lymphocyte precursor cells can be isolated and identified from bone marrow using a combination of an anti-CD34 antibody with one or more antibodies directed against surface antigens of the T lymphocyte. These antigens comprise CD2, CD5, CD7 and Leu 8. Preferably, the combination of antibodies comprises anti-CD34, anti-CD7 and anti-Leu 8.

In another embodiment of this invention, a population of later T lymphocyte precursor cells can be isolated and identified from bone marrow and/or thymus using an anti-CD34 antibody; more preferably, however, a combination of antibodies is used comprising anti-CD34 and anti-Leu 8 and one or more of anti-CD7, anti-CD5 and anti-CD2.

In still another embodiment of this invention, one can use a combination of antibodies to stage the development of thymocytes. A preferred combination of antibodies useful in identifying and isolating such cells comprises anti-CD34, anti-Leu 8, anti-CD1 and anti-CD3.

A preferred method of isolation is by means of multiparameter flow cytometric analysis using one or more antibodies described above. This method includes the analysis of both light scatter parameters as well as one or more fluorescence parameters. Other methods of isolation include magnetic bead based separation as previously described in U.S. Ser. No. 517,101.

Still another aspect of this invention is a method of therapy to treat T lymphocyte disorders and conditions. In such disorders, it may be desirable to alter the genetic makeup of T lymphocyte precursor cells isolated from the patient by means of genetic manipulation. In other instances, it may be desirable simply to isolate a population comprising such precursor cells. In both instances, it is preferred that the populations be substantially pure. In all instances, it may be desirable to expand the cells isolated in vitro prior to transplantation or transfusion to permit expansion and/or differentiation of the cells.

An additional aspect of this invention is in the monitoring of T lymphocyte recovery following any immuno-therapy. In this aspect of the invention, one or combinations of antibodies useful identifying the T lymphocyte precursor and/or stages thereof can be used to sample peripheral blood or lymphatic tissues for these cells.

DESCRIPTION OF THE INVENTION

Figure 1A:
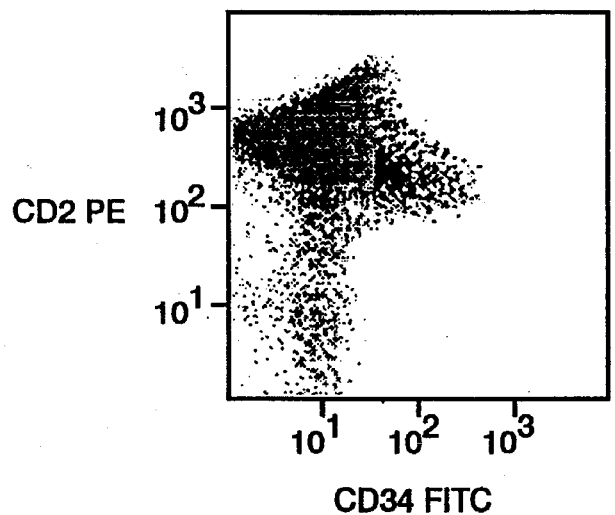
FIG. 1 comprises a series of dot plots of human thymocytes stained with anti-CD34 FITC and anti-CD2 PE monoclonal antibodies, wherein FIG. 1A comprises a plot of log PE versus log FITC fluorescence and FIG. 1B comprises a plot of transformed orthogonal light scatter versus forward light scatter.

The isolation and characterization of a population of T lymphocyte precursor cells was carried out as follows. Fetal specimens were obtained from aborted fetuses 17–25 weeks of gestational age and used following the guidelines of the Institutional Review Board of Stanford University Medical Center on the use of Human Subjects in Medical Research. Bone marrow cells were isolated by flushing intramedullary cavities of the femurs with RPMI 1640 (Gibco) with 10% fetal calf serum ("FCS") followed by NH$_4$Cl lysis. Other bone marrow aspirates were obtained from consenting normal adult volunteers. Bone marrow cell preparations were obtained using NH$_4$Cl lysates or density dependent centrifugation. Thymocytes were obtained from fetal thymi and pathologically normal thymi obtained from one month to two year old pediatric patients undergoing cardiac surgery. Whole thymic lobes were gently minced over #304 steel screen (Tylenter) in RPMI 1640 with 10% bovine calf serum. The collected thymocytes were washed twice with RPMI 1640.

Flow cytometric analysis was performed either on a FACScan™ flow cytometer or a FACStar™ Plus cell sorter (both available from Becton Dickinson Immunocytometry Systems, "BDIS"). Data acquisition was performed with FACScan Research software and FACStar Plus software (BDIS). Forward light scatter, orthogonal light scatter and three fluorescence signals were determined for each cell and stored in listmode data files. Each experiment measured approximately 30,000 cells. The analysis of the listmode data files was performed with Paint-A-Gate™ software (BDIS). (See U.S. Pat. No. 4,845,653). To increase the orthogonal light scattering resolution, the orthogonal light scattering signals were transformed by using a polynomial function as described in co-pending U.S. patent application Ser. No. 517,096. For light microscopic examination, 10,000 sorted cells were centrifuged for five minutes at 200 g and resuspended in 100 μl RPMI 1640 containing 10% FCS. Cytospin preparations were made on a Shandon cyto-centrifuge (Southern Product Ltd.). Slides containing sorted cells were stained with Wright Giemsa stain (Sigma).

Erythrocyte lysed bone marrow aspirates and thymi were stained with antibodies using a variety of monoclonal antibodies available from BDIS. Antibodies were fluorescently labelled with one of the following fluorochromes: phycoerythrin ("PE") fluorescein isothiocyanate ("FITC") and peridinin chlorophyll complex ("PerCp"). For a description of PE and PerCp, see U.S. Pat. Nos. 4,520,110 and 4,876,190 respectively. The monoclonal antibodies used were: anti-CD1 PE; anti-CD2 PE; anti-CD3 FITC, PE or PerCp; anti-CD4 FITC, PE or PerCp; anti-CD5 PE; anti-CD7 FITC or PE; CD10 PE; anti-CD11b PE; anti-CD13 PE; anti-CD19 PE; anti-CD20 PE; anti-CD25 PE; anti-CD33 PE; anti-CD34 FITC or PerCp; anti-CD38 FITC or PE; anti-CD44 biotin; anti-CD45 PE; anti-CD45RA PE; anti-CD49b biotin; anti-CD71 FITC or PE; anti-HLA DR FITC; anti-TCR 1 α/β FITC and anti-TCR 1 γ/δ FITC or PE. (All antibodies commercially available from BDIS except anti-CD44 which was obtained from Louis Picker, University of Texas Southwestern Medical Center).

As used herein, the designation of $^+$ or $^-$ is intended to mean "positive" or "negative" as the context permits. In other instances, $^{+++}$, $^{++}$ and $^+$ are intended to indicate levels of antigen expression with three "+" being the highest level of expression.

Figure 1B:
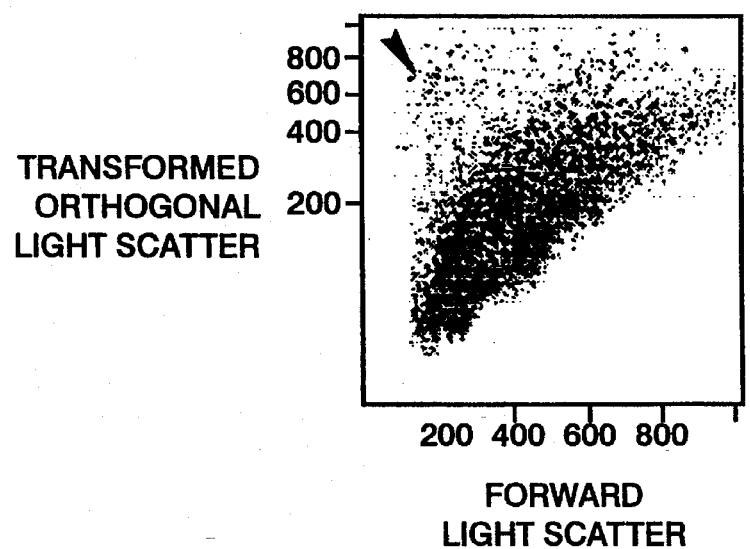

Initially, normal post-natal CD2$^+$ thymocytes were analyzed for their expression of CD34 which is associated with progenitor cells in other lineages. FIG. 1 shows a typical example of such an analysis with FIG. 1A illustrating the correlative expression of CD34 FITC and CD2 PE. FIG. 1B shows the correlative display of forward and orthogonal light scattering. A small population of cells is discernible with relatively large light scattering signals and which coexpress the CD2 and CD34 antigens. These cells are depicted black by simultaneous analysis of all four parameters, whereas all other cells remain gray.

Not all cells in the thymocyte suspension expressed the CD2 antigen. See FIG. 1A. These cells were identified either as B lymphocytes (i.e., CD2$^-$/CD19$^+$), myeloid cells (i.e., CD2$^-$/CD13$^+$) or erythrocytes. The erythrocytes displayed low forward and high orthogonal light scattering (arrow in FIG. 1B), and were definitively identified as such by morphologic examination of sorted cells.

The CD34$^+$/CD2$^+$ and CD34$^-$/CD2$^+$ subsets were sorted and stained for morphological analysis. In keeping with their light scattering properties, the CD34$^+$ thymocytes comprised a homogeneous population of large "atypical" blasts with prominent nucleoli, equally dispersed chromatin and a cytoplasm with some nuclear clearing. This morphology is quite similar to that seen in early progenitor cells of other lineages. In contrast, the CD34$^-$/CD2$^+$ thymocytes were smaller, and showed distinct lymphold characteristics.

Figure 2A:
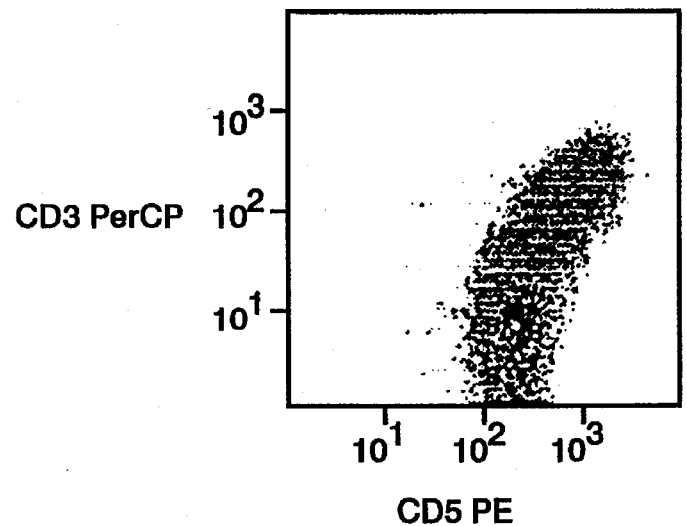
FIG. 2 comprises a series of dot plots of log PerCp versus log PE for human thymocytes stained with (A) anti-CD34 FITC, anti-CD5 PE, anti-CD3 PerCp and (B) anti-CD34 FITC, anti-CD4 PE and anti-CD8 PerCp (with CD34$^+$ cells depicted in black) wherein the arrow indicates the direction of T lymphocyte differentiation.
Figure 2B:
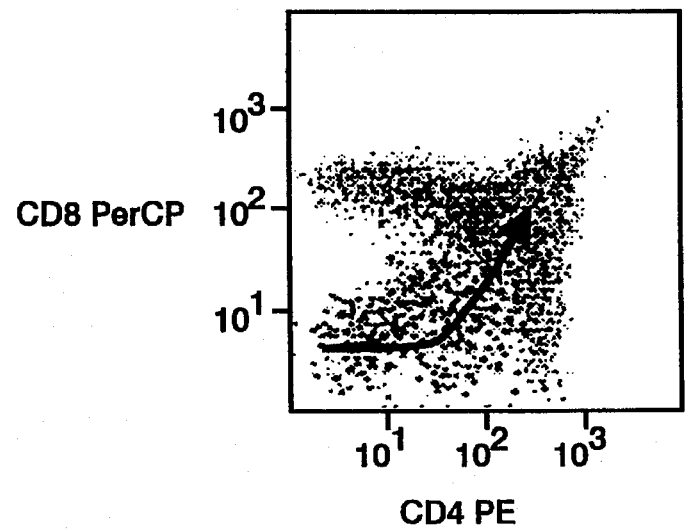

The expression of the CD34 antigen on human thymocytes and their blast morphology strongly suggested that this cell population represented the earliest T lymphocyte present in human thymi. Further evidence that these cells are, in fact, the earliest T lineage population in the thymus was obtained in three color immunofluorescence experiments in which the CD34 antigen was examined in conjunction with the CD5 and CD3 antigens, see FIG. 2A, and the CD4 and CD8 antigens, see FIG. 2B. In FIG. 2A, all CD34$^+$ thymocytes (which are depicted black) show an immature CD5$^{++}$/CD3$^-$ phenotype. FIG. 3B discloses that the black colored CD34$^+$ thymocytes only partly expressed the CD4 and CD8 antigens. About half the CD34$^{+++}$ thymocyte populations are CD4$^-$, CD8$^-$; about a third are CD4$^+$, CD8$^-$; while the remainder show the CD4$^+$, CD8$^+$ phenotype typical of cortical thymocytes.

A detailed antigenic profile of the CD34$^+$ thymocytes was assessed by correlating the expression of the CD34 antigen with other antigens. FIGS. 3A–3F illustrates typical patterns of correlated expression of the CD34 antigen with the CD4, CD8, CD1, CD10, CD7 and Leu 8 antigens respectively. (As previously defined, the CD34$^+$ thymocytes are depicted as black while all other cells are depicted as gray.)

Figure 3A:
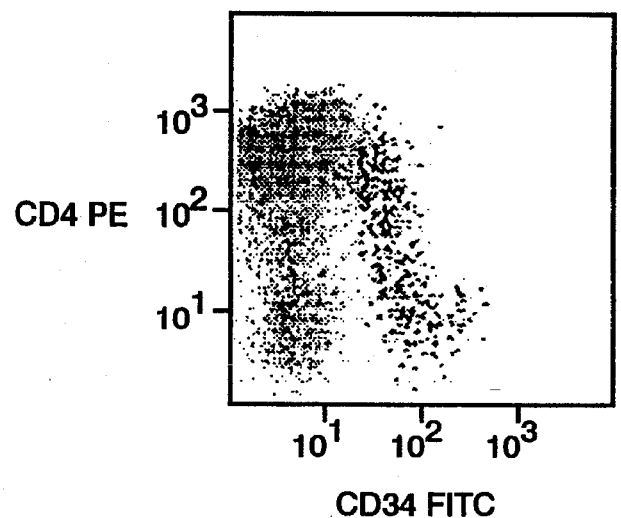
FIG. 3 comprises a series of log fluorescence dot plots for thymocytes stained with anti-CD34 FITC and one of the following PE labelled antibodies: (A) anti-CD4, (B) anti-CD8, (C) anti-CD1, (D) anti-CD10, (E) anti-CD7 and (F) anti-Leu 8 antibodies wherein the CD34$^+$ cells are depicted in black.
Figure 3B:
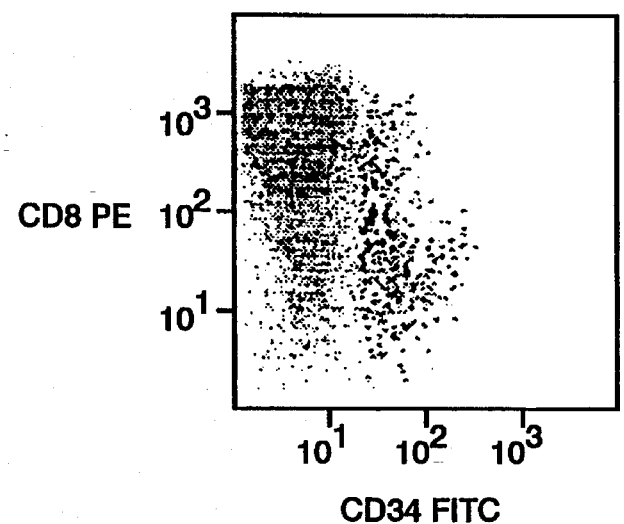

FIG. 3A shows that the CD34$^{+++}$ thymocytes are CD4$^-$, and as CD34 expression decreases on a per cell basis there is a correlated up-regulation of CD4. This nearly linear relationship between the expression of CD34 and CD4 was apparent in all thymi examined. In FIG. 3B, the CD34$^+$ subset is demonstrated to be largely CD8$^±$ with only a small portion of the CD34$^+$ cells expressing this antigen. This inversely correlated expression of the CD4 and CD8 antigens with the progenitor cell marker, CD34, strongly suggests a pathway of T lymphocyte differentiation in which a CD34$^{+++}$/CD4$^-$/CD8$^-$ prothymocyte emigrant from the bone marrow begins to down-regulate CD34 and up-regulate CD4 upon entry into the thymus. CD8 antigen is acquired on a CD34$^+$/CD4$^+$ cell, and marks the transition to the common cortical thymocyte phenotype. This differentiation pathway is indicated by the arrow in FIG. 2B.

Figure 3C:
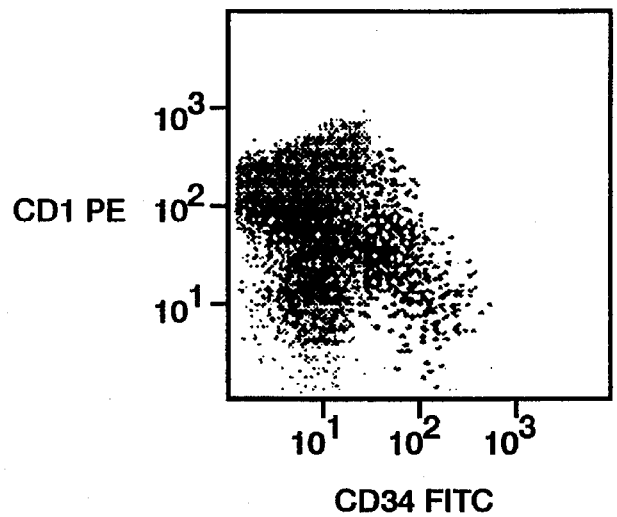
Figure 3D:
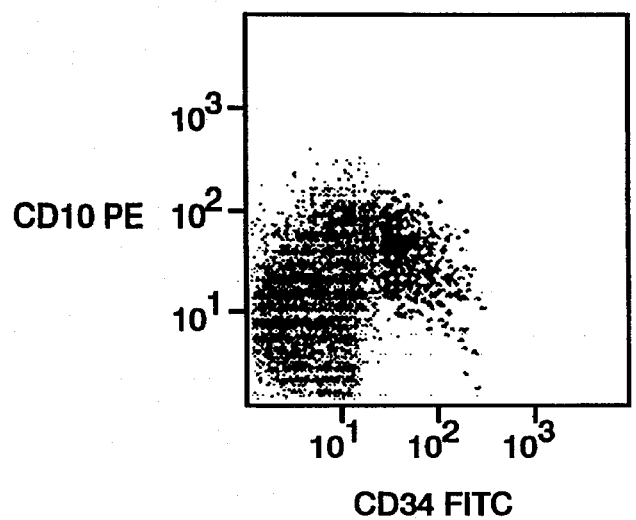
Figure 3E:
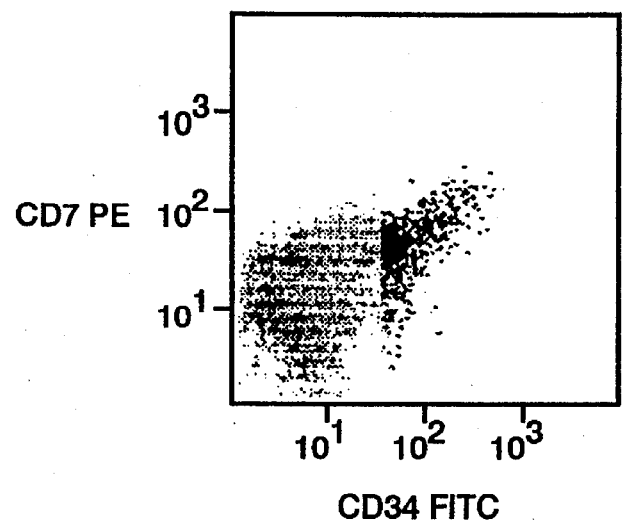
Figure 3F:
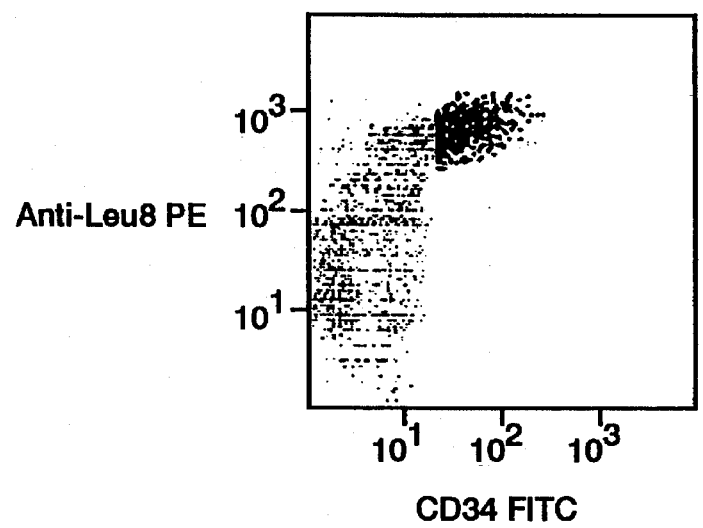
Figure 4A:
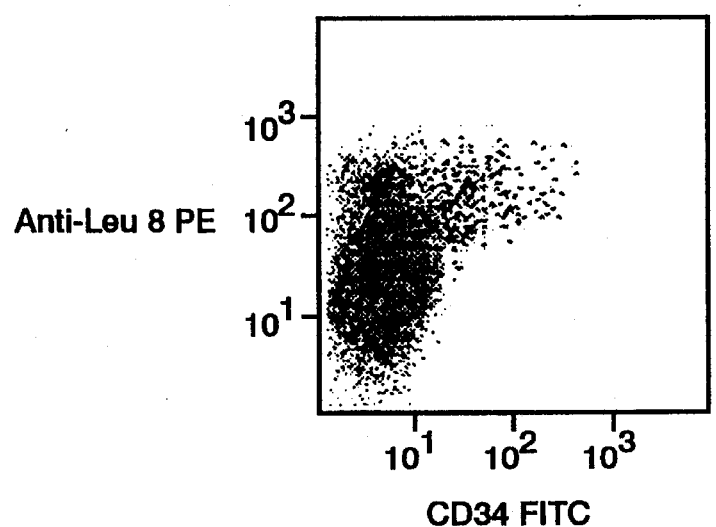
FIG. 4 comprises a series of log fluorescence dot plots of human thymocytes stained with (A–C) anti-CD34 FITC, anti-Leu 8 PE and unconjugated anti-CD3 (surface) and anti-CD3 PerCp (cytoplasmic) or (D) anti-CD34 FITC, anti-Leu 8 PE and an irrelevant IgG PerCp control (wherein the CD34$^+$ cells are depicted in black).
Figure 4B:
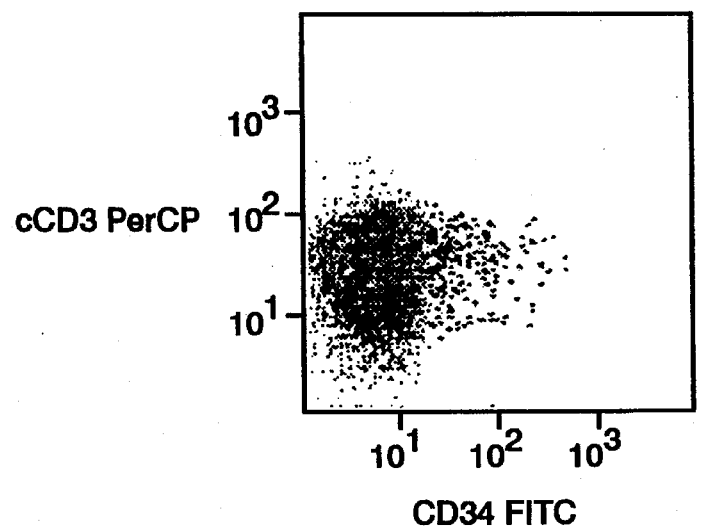
Figure 4C:
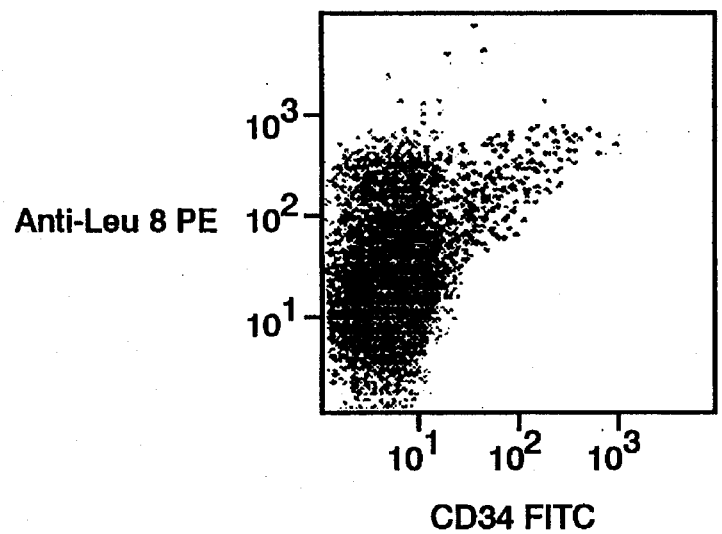
Figure 4D:
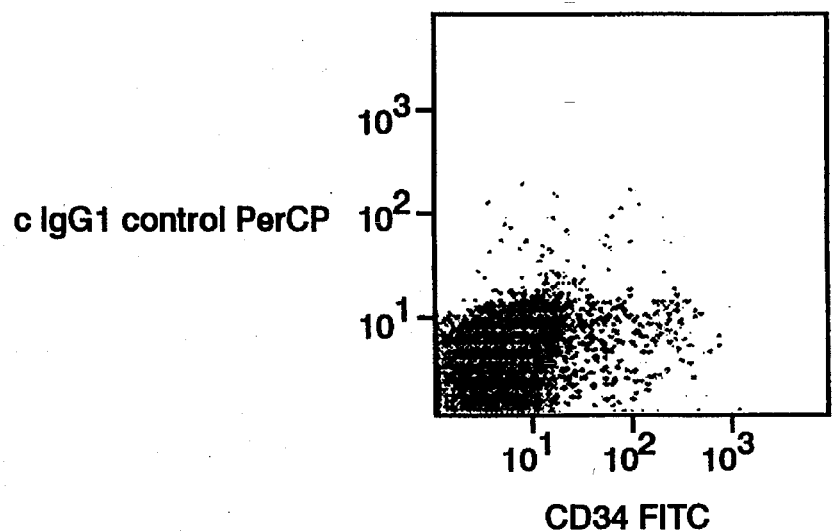
Figure 5A:
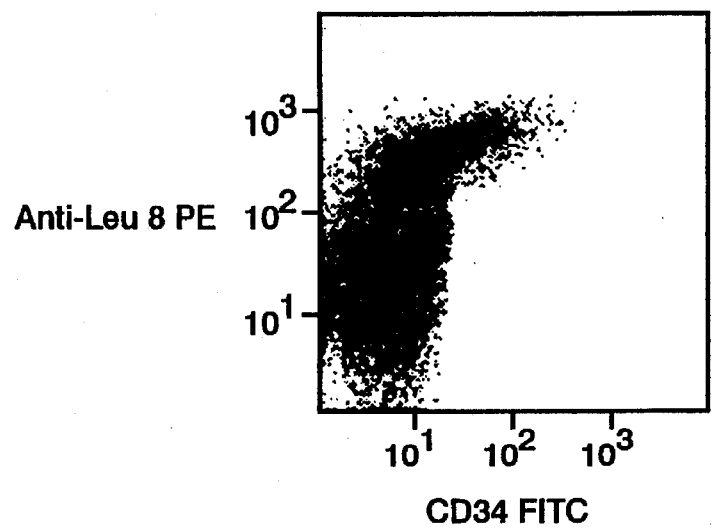
FIG. 5 comprises a series of (A–C, E–F) log fluorescence dot plots and (D, H) transformed orthogonal light scatter versus forward light scatter for human thymocytes stained with (A–B, E–F) anti-CD34 FITC, anti-Leu 8 PE and anti-CD3 PerCp and with (C, G) anti-CD34 FITC, anti-CD1 PE and anti-CD3 PerCp wherein each stage of differentiation was assigned a different color: T I black; T I light blue; T III violet; T IV yellow; T V red; T VI blue; and T VII green.
Figure 5B:
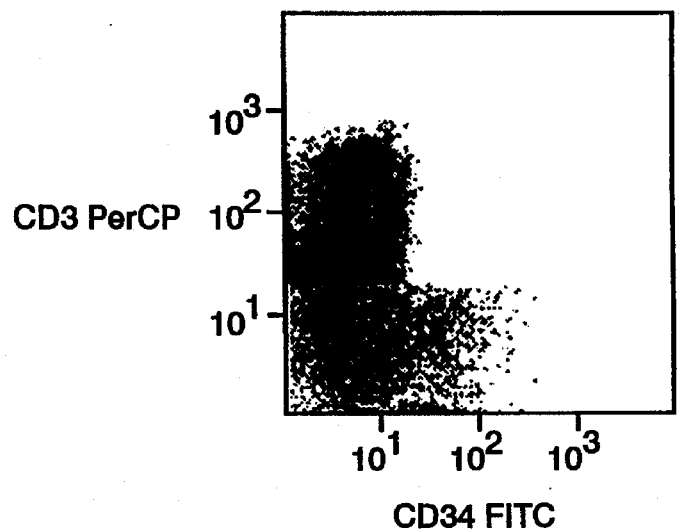
Figure 5C:
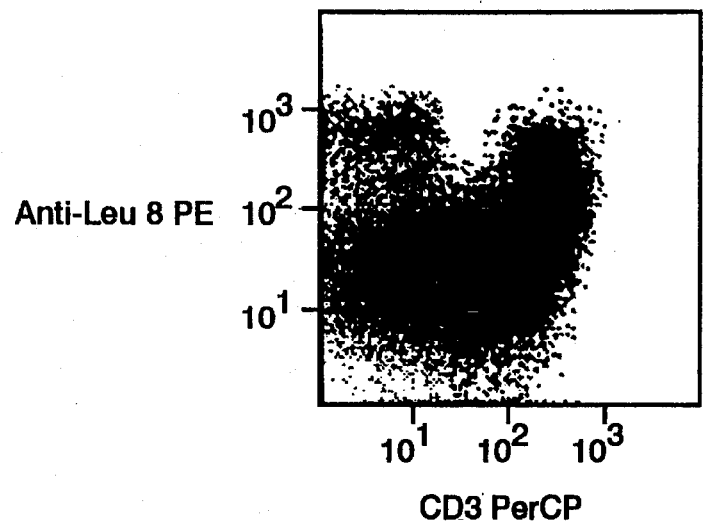
Figure 5D:
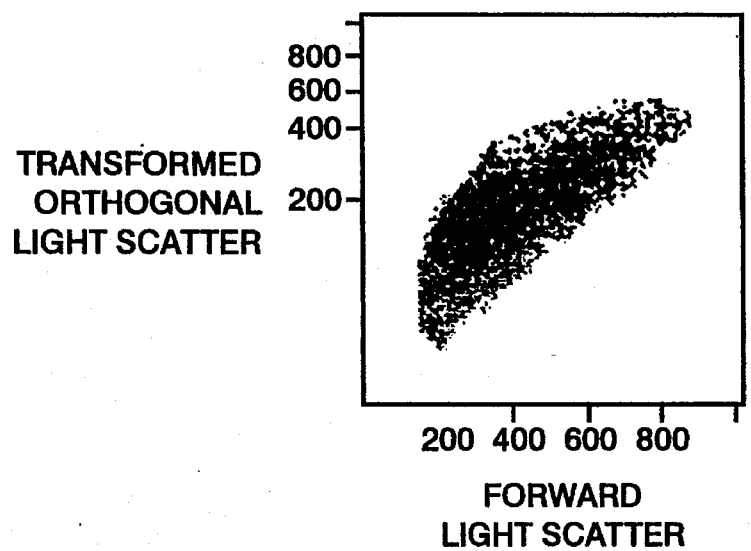
Figure 5E:
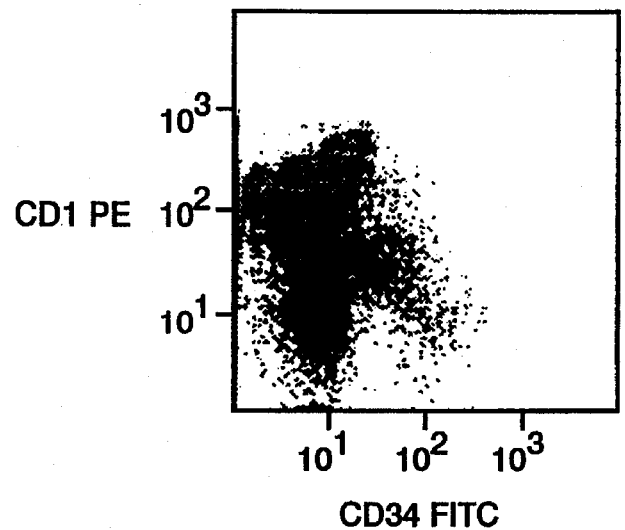
Figure 5F:
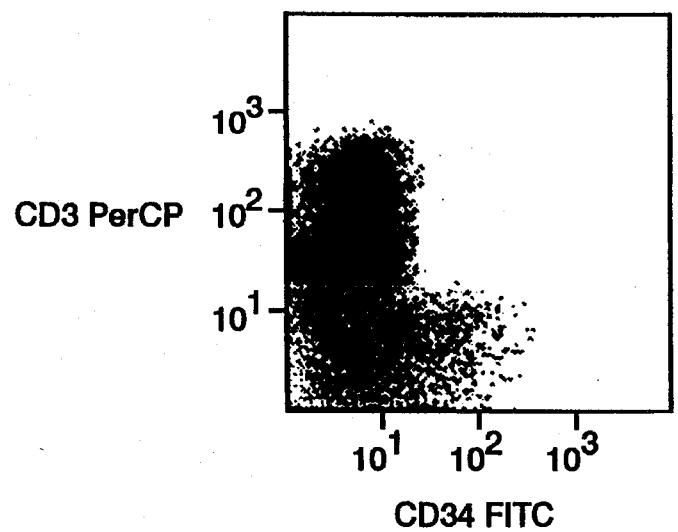
Figure 5G:
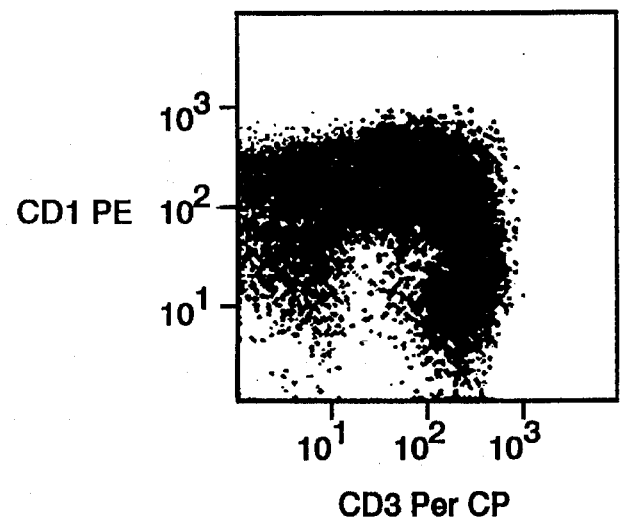
Figure 5H:
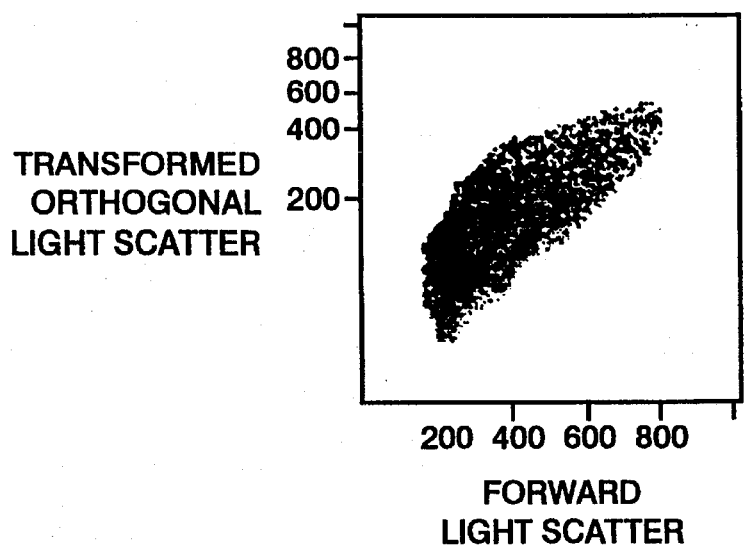

FIGS. 3C and 4D show that the CD1 and CD10 expression is also inversely correlated with CD34 expression. CD34$^{+++}$ cells are weak to negative for these antigens, whereas CD34$^+$ thymocytes are moderate to bright. In contrast to CD1, CD4, CD8 and CD10, the expression of CD7 and Leu 8 antigens are directly correlated with CD34. Both antigens are highly expressed on the CD34$^+$ subset, but these levels decrease proportionally with the decrease in CD34 expression.

Expression of cytoplasmic CD3 has been shown to precede the surface appearance of this antigen. To investigate whether cytoplasmic CD3 was present in the CD34$^+$ thymocytes, cytoplasmic antigen staining techniques were adapted for flow cytometry. Cell surface CD3 was blocked with unconjugated anti-CD3 antibody concomitantly with staining of the cells with anti-CD34 FITC and anti-Leu 8 PE. After fixation, the cell membrane was permeablized with Triton X-100 and the cell suspension was incubated with anti-CD3 PerCp. See FIGS. 4A/4B. In a control experiment, the cell surface was blocked with an irrelevant antibody and intra-cytoplasmic staining was performed with a PerCp conjugate of the irrelevant antibody. See FIGS. 4C/4D. In both experiments, the CD34$^+$ thymocytes expressed the Leu 8 antigen brightly (and are shown in black, whereas all other cells are shown in gray). In the cytoplasm of all thymocytes, including the entire CD34$^+$ subset, cCD3 was present, whereas in the control experiment non-staining was found of the irrelevant PerCp-conjugated antibody.

The CD34$^+$ thymocyte subset was examined for expression for a total of 23 different leukocyte antigens. In addition to the reactivities discussed above, it was determined that CD11$b$, CD13, CD19, CD25, CD33, CD71, TCR α/β and TCR γ/δ were not expressed on the CD34$^+$ thymocytes; that CD44, CD54 and HLA-DR (like CD1, CD4, CD8 and CD10) were partially expressed on CD34$^+$ thymocytes; and that CD2, CD5, CD7, Leu 8, CD38, CD45, CD45RA and CD49$d$ were expressed on all CD34$^+$ thymocytes. To address the extent of inter-donor variation and the relative occurrence of these antigens on human thymocytes, in general, and the CD34$^+$ subset, in particular, their presence was

TABLE I

|   |     | CD34 | CD1     | CD2     | CD3   | CD4   | CD5     | CD7     | CD8   |
|---|-----|------|---------|---------|-------|-------|---------|---------|-------|
| F | AGE |      |         |         |       |       |         |         |       |
| 1 | 17  | 2.6  | 84/61   | 100/100 | 31/0  | ND    | 100/100 | 100/100 | ND    |
| 2 | 21  | 1.2  | 89/84   | 100/100 | 34/0  | ND    | 100/100 | 100/100 | ND    |
| 3 | 21  | 2.1  | 80/62   | 100/100 | 50/0  | 93/ND | 100/100 | 100/100 | 84/ND |
| 4 | 25  | 2.0  | 85/57   | 100/100 | 39/0  | ND    | 100/100 | 100/100 | ND    |
|   | mean| 2.0  | 85/61   | 100/100 | 39/0  |       | 100/100 | 100/100 |       |
|   | SD  | 0.6  | 3.7/2.9 | 0/0     | 8.3/0 |       | 0/0     | 0/0     |       |
| P | AGE[b] |   |         |         |       |       |         |         |       |
| 1 | 1   | 0.6  | 74/75   | 100/100 | 57/0  | 90/67 | 100/100 | 100/100 | 81/50 |

TABLE I-continued

| | | | | | | | | | |
|---|---|---|---|---|---|---|---|---|---|
| 2 | 3 | 3.5 | 91/74 | 100/100 | 55/0 | 91/65 | 100/100 | 100/100 | 85/48 |
| 3 | 4 | 1.8 | 90/52 | 100/100 | 55/0 | 92/61 | 100/100 | 100/100 | 87/79 |
| 4 | 6 | 1.5 | 93/92 | 100/100 | 46/0 | 90/52 | 100/100 | 85/85 | 84/50 |
| 5 | 6 | 1.2 | 90/93 | 100/100 | 39/0 | 87/75 | 100/100 | 100/100 | 86/72 |
| 6 | 12 | 1.1 | 92/99 | 100/100 | 47/0 | 79/55 | 100/100 | 100/100 | 87/45 |
| 7 | 24 | 0.7 | 84/71 | 99/100 | 42/0 | 79/75 | 98/100 | 100/100 | 82/43 |
| 8 | 24 | 0.3 | 90/80 | 98/97 | 75/0 | 90/43 | 100/100 | 100/100 | 89/66 |
| 9 | 24 | 0.2 | 88/80 | 100/100 | 48/0 | 91/60 | 100/100 | 100/100 | 82/33 |
| | mean | 1.2 | 88/80 | 99/99 | 51/0 | 88/61 | 99/100 | 98/98 | 85/54 |
| | SD | 0.95 | 5.5/13 | 0.7/0.9 | 10/0 | 5/10 | 0.6/0 | 4.7/4.7 | 3/14 |

| | | CD10 | CD11b | CD13 | CD19 | CD38 | Leu 8 | HLA-DR |
|---|---|---|---|---|---|---|---|---|
| F | AGE | | | | | | | |
| 1 | 17 | 11/67 | ND | 0.4/0 | ND | 100/100 | 56/100 | 13/69 |
| 2 | 21 | ND | ND | ND | 1.1/0 | 100/100 | 47/98 | ND |
| 3 | 21 | 20/55 | ND | 0.5/0 | ND | 100/100 | 62/100 | 25/44 |
| 4 | 25 | 14/70 | ND | 0.2/0 | ND | 100/100 | 64/100 | 20/44 |
| | mean | 15/64 | | 0.4/0 | | 100/100 | 57/100 | 19/52 |
| | SD | 4.6/7.9 | | 0.2/0 | | 0/0 | 7.6/1 | 6.0/14 |
| P | AGE[b] | | | | | | | |
| 1 | 1 | 23/50 | 0.9/0 | 0.7/0 | 0.6/0 | 100/100 | 35/100 | 57/95 |
| 2 | 3 | 28/90 | ND | ND | ND | 100/100 | 60/100 | 58/100 |
| 3 | 4 | 29/70 | ND | ND | ND | 100/100 | 64/100 | ND |
| 4 | 6 | 14/56 | 0.3/0 | 0.1/0 | 0.8/0 | 100/100 | ND | 54/51 |
| 5 | 6 | 19/73 | 0.4/0 | 0.5/0 | 0.7/0 | 100/100 | 31/100 | 62/86 |
| 6 | 12 | 21/81 | 0.2/0 | 0.2/0 | 0.4/0 | 100/100 | ND | 55/67 |
| 7 | 24 | 21/78 | 0.2/0 | 0.3/0 | 0.9/0 | 98/100 | 58/100 | 38/87 |
| 8 | 24 | 23/70 | 0.1/0 | 0.3/0 | 0.2/0 | 100/100 | 34/100 | 54/96 |
| 9 | 24 | 20/67 | 0.5/0 | 0.3/0 | 0.3/0 | 100/100 | 30/100 | 55/86 |
| | mean | 22/71 | 0.4/0 | 0.3/0 | 0.6/0 | 99/100 | 45/100 | 54/84 |
| | SD | 4.3/12 | 0.2/0 | 0.2/0 | 0.2/0 | 0.6/0 | 14/0 | 7/16 |

[a] = gestational weeks
[b] = months from birth determined on 9 pediatric ("P") and 4 fetal ("F") thymi. See Table I. The age of the patients at which the thymi were removed is indicated.

The sequential acquisition and loss of antigens in concordance with changes in light scattering properties was used to asses a differentiation pathway followed by T lymphocytes in human thymi. Various combinations of three antigens in addition to forward and orthogonal light scattering signals were applied on human thymocyte suspensions in order to assess the optimal combination to describe T lymphocyte differentiation. A total of 4 markers (CD34, CD3, Leu8, and CD1) applied in 2 combinations of 3 markers each (CD34, CD3 and Leu 8; and CD34, CD3 and CD1) were found to clearly and reproducibly describe the entire range of thymocyte differentiation.

FIGS. 5A–5D shows a typical example of a five parameter measurement correlating forward, orthogonal light scattering and the expression of CD34, CD3 and Leu 8 antigens, whereas in FIGS. 5E–5H a typical example of forward, orthogonal light scattering and the CD34, CD3 and CD1 antigens is shown. Seven differentiation stages are identified by multidimensional flow cytometric analysis, each stage is represented by a color.

In the thymus, the earliest T cell differentiation stage, T I, is represented by a black color and only discernible in the right panels of the figure. This stage is characterized by the presence of CD34, absence of CD1 and CD3 and large light scattering signals. The second differentiation stage, T II, is depicted light blue in the right panels and is characterized by the presence of both CD34 and CD1, the absence of CD3 and large light scattering signals. Both early T cell differentiation stages, T I and T II, are depicted light blue in the left panels and brightly express the Leu 8 antigen (i.e., Leu 8$^{+++}$). The third differentiation stage, T III, is depicted violet in both panels and is characterized by the bright expression of Leu 8, a dim expression of CD1 (i.e., CD1$^{+}$), the absence of CD34 and CD3 and low light scattering signals. The fourth differentiation stage, T IV, is depicted yellow in both panels and characterized by the bright expression of CD1, a decreasing expression of the Leu 8 antigen, the absence of CD34 and CD3 and low light scattering signals. The fifth differentiation stage, T V, is depicted red in both panels and characterized by the bright expression of the CD3 antigen, and low as well as large light scattering signals. The sixth differentiation stage, T VI, is depicted blue in both panels and characterized by the absence of CD34, an intermediate expression of both CD1 and Leu 8 (i.e., CD1$^{++}$), bright expression of the CD3 antigen and low light scattering signals. The most mature T cell differentiation identified, stage T VII, is depicted green in both panels and characterized by the bright expression of the Leu 8 and CD3 antigens, the absence of CD34 and CD1 and low light scattering signals. Note the remarkable reciprocal appearance of the CD1 and Leu 8 antigens during T cell differentiation in human thymi as discernible when comparing the left and right panels of FIG. 5.

Figure 6A:
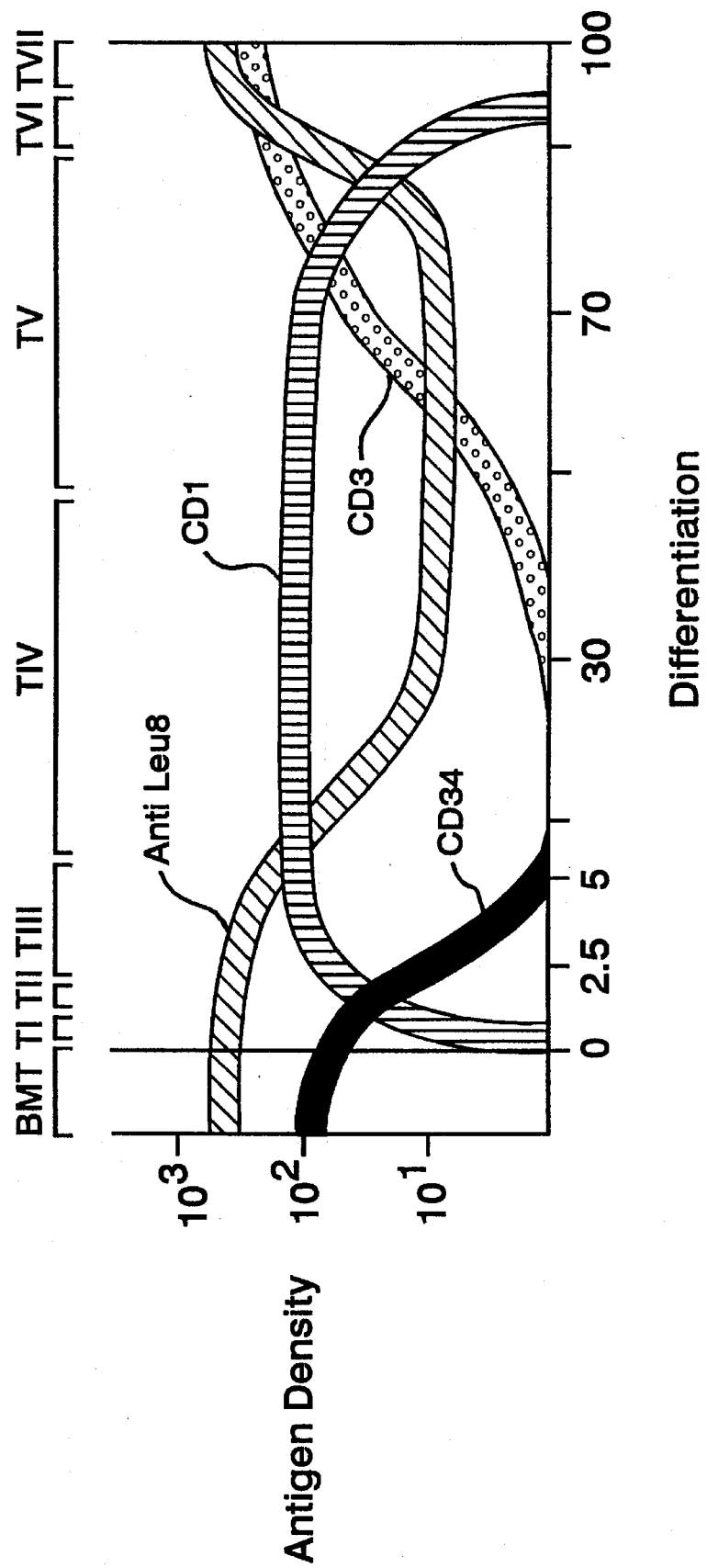
FIG. 6 comprises three schematic representations of the T lymphocyte differentiation pathway as defined by (A) the antigens CD1, CD3, CD34 and Leu 8 with log antigen density on the abscissa and the stage of differentiation (from FIG. 5) on the ordinate.

The percentages of thymocytes present in each T cell differentiation stage was determined in six pediatric thymi and four fetal thymi. See Table II. Table II shows a remarkable consistency of the frequency of the thymocytes categorized in each stage. A schematic representation of the T cell differentiation as defined by CD34, CD3, CD1 and Leu 8 expression is shown in FIG. 6A. On the vertical axis the antigen density is given, the relative proportion of each of the seven differentiation stages is given along the horizontal

TABLE II

|   | | T I | T II | T III | T IV | T V | T VI | T VII |
|---|---|---|---|---|---|---|---|---|
| F AGE[a] | | | | | | | | |
| 1 | 17 | 1.0 | 1.6 | 4.8 | 62.0 | 15.6 | 10.3 | 4.7 |
| 2 | 21 | 0.4 | 0.8 | 4.2 | 60.8 | 18.2 | 9.2 | 6.4 |
| 3 | 21 | 0.8 | 1.3 | 7.4 | 40.7 | 31.8 | 11.4 | 7.1 |
| 4 | 25 | 0.6 | 1.4 | 3.8 | 55.7 | 25.5 | 5.2 | 7.8 |
| | mean | 0.7 | 1.3 | 5.1 | 54.8 | 22.8 | 9.0 | 6.5 |
| | SD | 0.3 | 0.3 | 1.6 | 9.8 | 7.3 | 2.7 | 1.3 |
| P AGE[b] | | | | | | | | |
| 1 | 1 | 0.2 | 0.5 | 5.0 | 41.5 | 37.2 | 6.3 | 8.5 |
| 2 | 3 | 1.7 | 1.8 | 2.9 | 43.9 | 37.0 | 4.9 | 7.7 |
| 3 | 4 | 1.4 | 1.3 | 1.3 | 42.4 | 46.0 | 3.0 | 5.0 |
| 4 | 24 | 1.4 | 0.9 | 0.8 | 47.6 | 35.8 | 8.3 | 5.1 |
| 5 | 24 | 0.3 | 0.4 | 1.8 | 39.5 | 50.0 | 6.2 | 1.8 |
| 6 | 24 | 0.5 | 0.3 | 6.1 | 44.7 | 42.6 | 2.9 | 3.1 |
| | mean | 0.9 | 0.9 | 3.0 | 43.3 | 41.4 | 5.3 | 5.2 |
| | SD | 0.6 | 0.5 | 1.9 | 2.6 | 5.2 | 1.9 | 2.6 |

[a] = gestational weeks
[b] = months from birth axis. This T cell differentiation scheme was used to study the presence of other antigens in each of the stages.

Figure 6B:
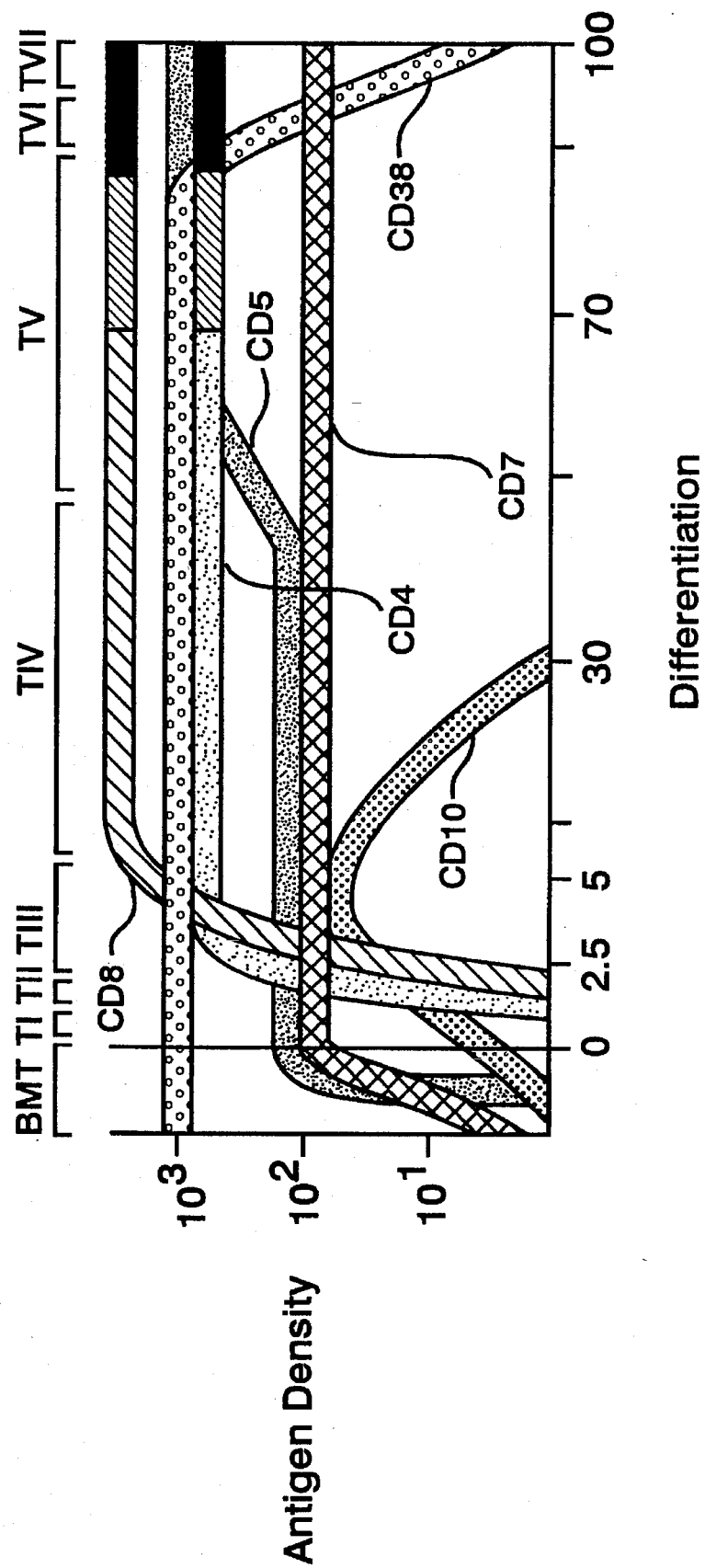

To determine "other" antigen expression associated with the stages, T I–T VII, three color immunofluorescence experiments were performed in which one of the differentiation determining antigens was exchanges for the antigen studied. The expression of the CD4, CD5, CD7, CD8, CD10 and CD38 antigens are presented in the differentiation scheme in FIG. 6B. The changes in the hatching in the representation of the CD4 and CD8 antigens represent the point at which one of the antigens is losing density in the differentiation of double positive (CD4$^+$/CD8$^+$) immature thymocytes to single positive mature T cells (either CD4$^+$ or CD8$^+$). The point at which only CD4 or CD8 is detectable is represented by the solid black line.

Figure 6C:
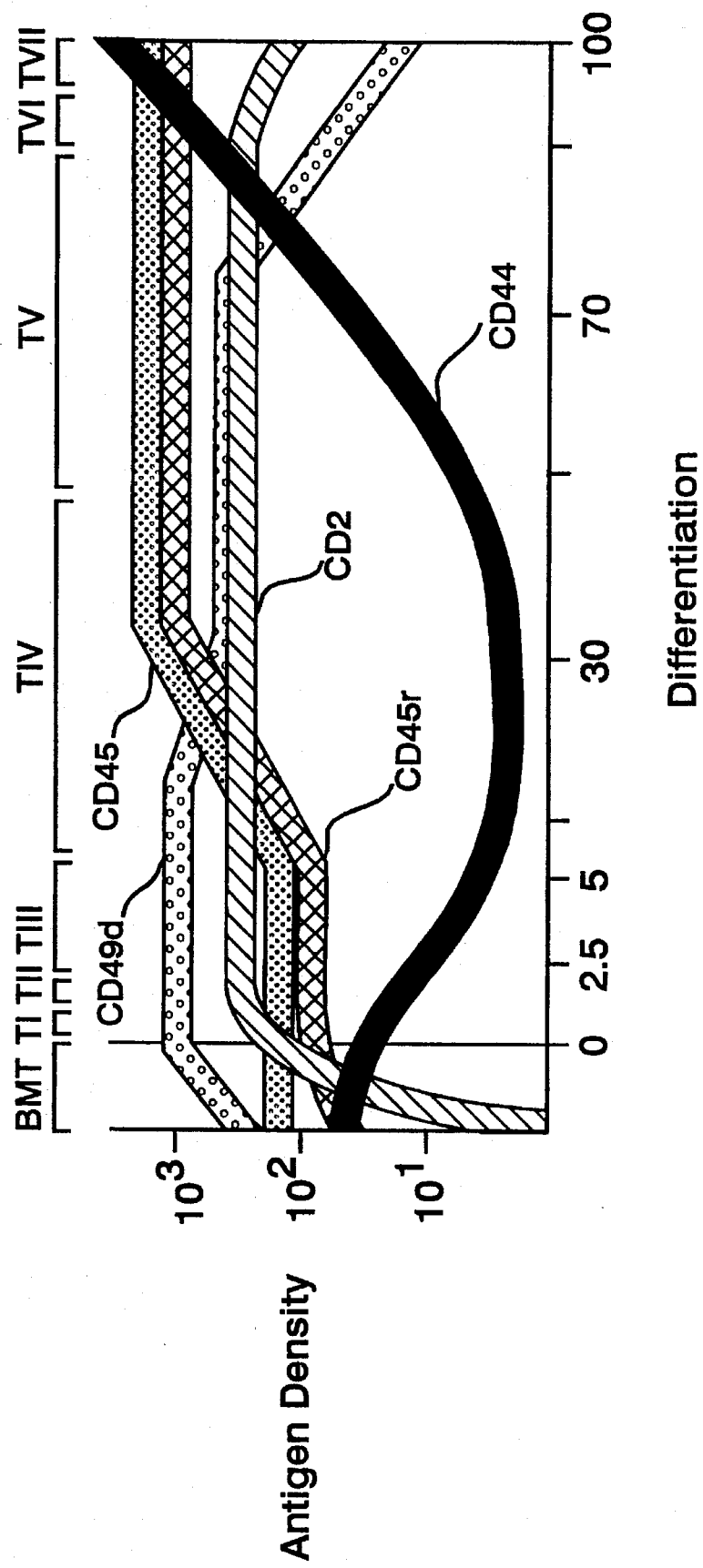

In FIG. 6C, the expression of CD45 and CD45RA epitopes on Leukocyte Common Antigen/T-200 molecules, and of the adhesion molecules CD2, CD44 and CD49$d$ are represented in the differentiation scheme. Other antigens examined but not shown in FIG. 6, include CD54, HLA-DR, CD25, and CD71. The CD54 antigen (ICAM-1) was expressed only dimly on part of the thymocytes throughout the T cell differentiation pathway. The HLA-DR antigen, although expressed on a significant amount of thymocytes, also showed no relation with T cell differentiation. CD25 expression was found only on a proportion of the late T cells stages T VI and T VII. The CD71 expression was found on a small proportion of thymocytes, but throughout the differentiation stages. In keeping with previous studies indicating the required co-translocation of CD3 and T cell antigen receptor (TCR) heterodimers to the cell surface, cell surface TCR αβ and γδ were not detected on thymocytes until cell surface CD3 was present. The overall frequency of TCR γ/δ-bearing cells was less than 2% in all specimens examined.

The knowledge of the antigenic profile and light scattering characteristics of the earliest T lymphocytes in human thymus permitted a guided exploration for earliest T lymphocytes in human bone marrow. Adult human bone marrow aspirates were stained with anti-CD34 PerCp, anti-Leu 8 PE and an early T cell antigen marker, either anti-CD2 FITC, anti-CD5 FITC or anti-CD7 FITC. In order to enrich for progenitor cells, bone marrow cells were acquired on a FACStar™ cell sorter with a light scattering gate excluding monocytes and neutrophils and with a threshold on CD34 fluorescence intensity. A small population of cells constituting less than 5% of the bone marrow CD34$^+$ cells coexpressed the CD2, CD5, CD7 and Leu 8 antigens. The CD34$^+$, CD2$^+$, CD5$^+$ and CD7 $^+$ cell population was only detectable in 5 of 15 marrow aspirates. Cell sorting revealed a morphologically heterogeneous population of blast cells, including cells with features of erythroblasts, myeloblasts, lymphoblasts, and morphologically undifferentiated blasts. These results indicate that in adult marrow, this population is unlikely to represent a homogeneous population of bone marrow T cell precursors. The heterogeneity of the cell population was further confirmed by additional experiments which showed that the CD13, CD33 and CD10 antigens were present on a variable number of CD34$^+$, CD2$^+$, CD5$^+$ and CD7$^+$ cells. The presence of a variety of cell lineages in the CD34$^+$, CD7$^+$ cell fraction implies that reliable detection of the earliest T cell precursors in adult bone marrow is extremely difficult if not impossible at this time.

Figure 7A:
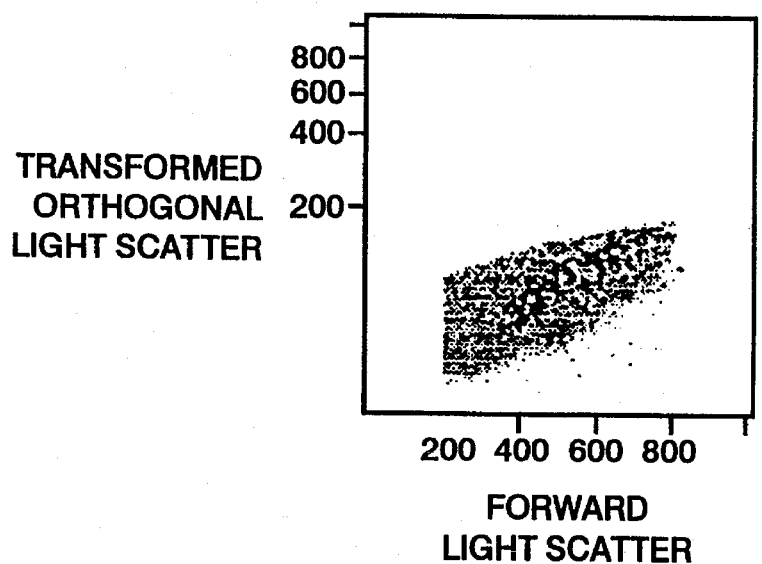
FIG. 7 comprises a series of dot plots of (A) transformed orthogonal light scatter versus forward light scatter and (B–D) log fluorescence for erythrocyte lysed fetal bone marrow cells labelled with anti-CD34 PerCp, anti-Leu 8 PE and anti-CD7 FITC wherein the CD34$^+$/CD7$^+$ cells are depicted in black.
Figure 7B:
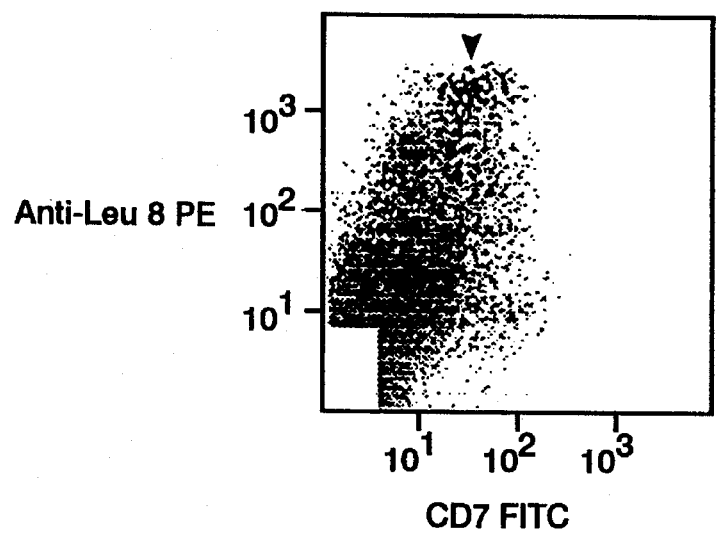
Figure 7C:
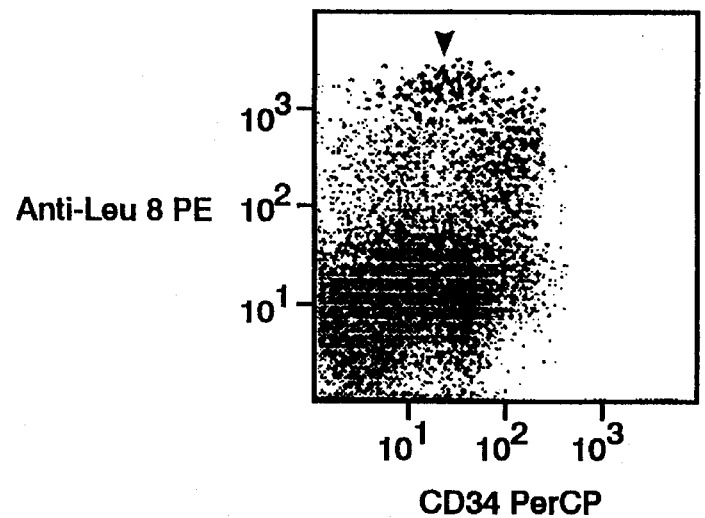
Figure 7D:
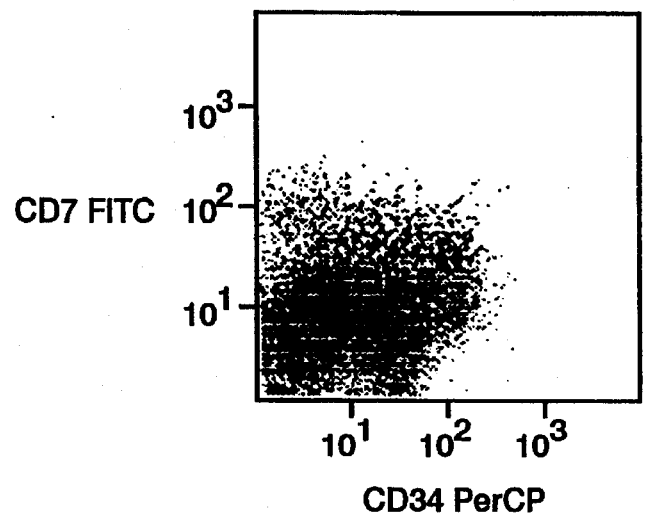
Figure 8A:
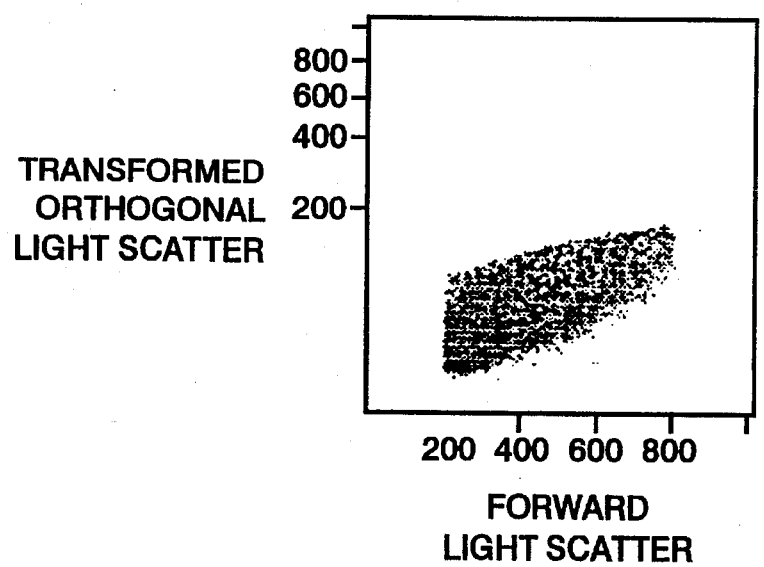
FIG. 8 comprises a series of dot plots of (A) transformed orthogonal light scatter versus forward light scatter and (B–D) log fluorescence for erythrocyte lysed fetal bone marrow cells labelled with anti-CD34 PerCp, anti-Leu 8 PE and anti-CD2 FITC wherein the CD34$^+$/CD2$^+$ cells are depicted in black.
Figure 8B:
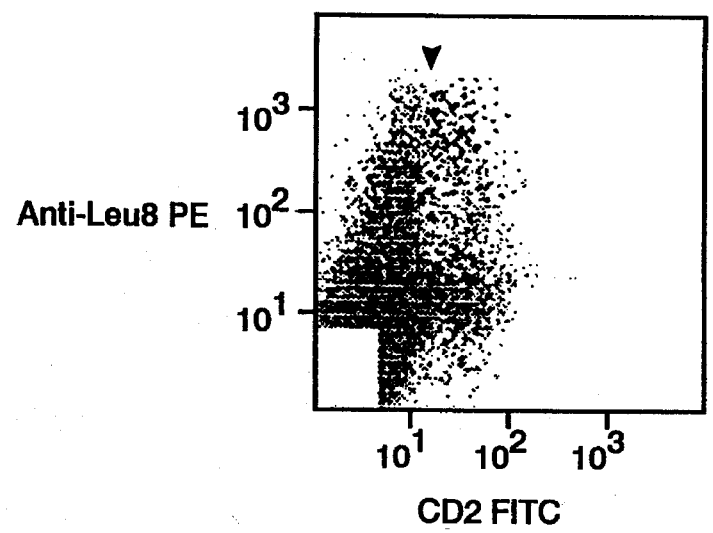
Figure 8C:
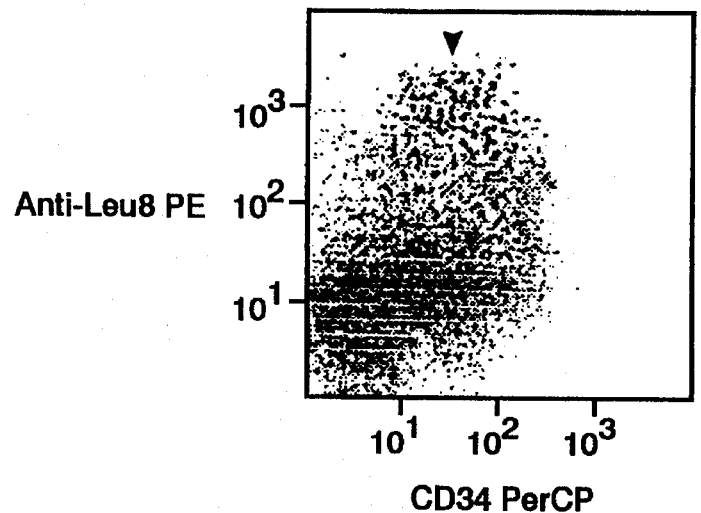
Figure 8D:
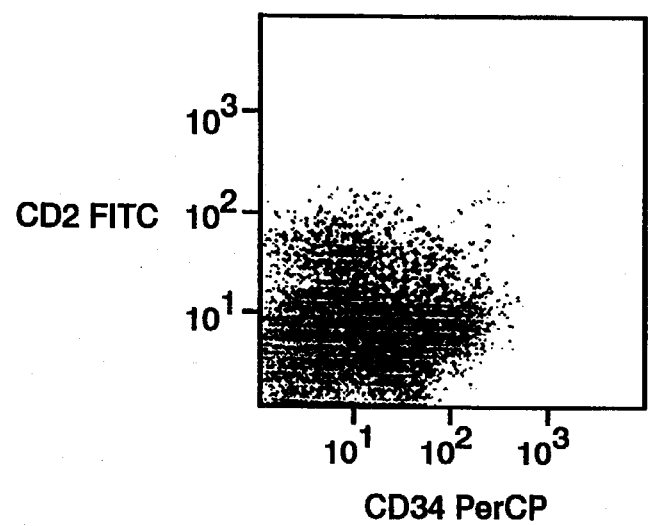

In contrast, in fetal specimens, populations strongly suggestive of the earliest T cell precursors could be readily identified. FIGS. 7A–7D illustrate a representative experiment of an analysis of a fetal bone marrow (gestational age—17 weeks) stained with anti-Leu 8 PE, anti-CD7 FITC and anti-CD34 PerCp. A forward and orthogonal light scatter gate (FIG. 7A) and a gate excluding CD7 , Leu 8 cells (FIG. 7B) was applied to increase the number of potential T cell precursors. In the figure, the CD34$^+$, CD7$^+$ cells all coexpressed the Leu 8 antigen but with varying intensities (FIGS. 7B and 7C). The brightest Leu 8$^+$ T cell precursors showed similar characteristics as the earliest thymocyte population (compare with FIGS. 5A–5D) and are indicated with arrows in the figure. The black colored cells which expressed the Leu 8 antigen with lesser intensity expressed a higher density of the CD34 antigen (FIG. 7B). Since in other lineages the intensity of CD34 is directly related to the degree of immaturity, this suggests that these cells are of earlier origin. See U.S. Ser. No. 717,101.

Figure 9A:
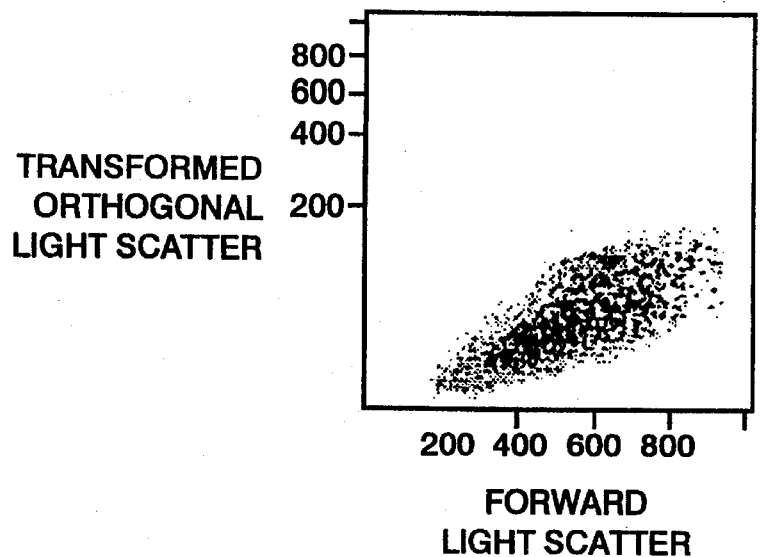
FIG. 9 comprises a series of dot plots of (A) transformed orthogonal light scatter versus forward light scatter and (B–D) log fluorescence for erythrocyte lysed fetal bone marrow cells labelled with anti-CD34 PerCp, anti-CD3 PE and anti-CD7 FITC wherein the CD34$^+$/CD7$^+$ cells are depicted in black.
Figure 9B:
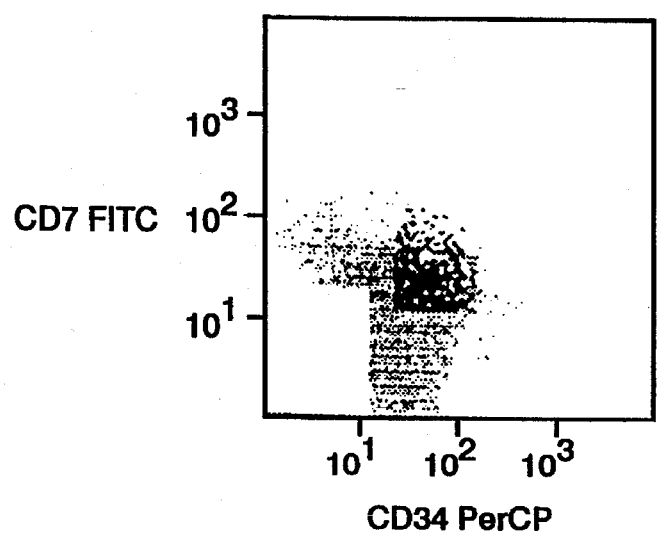
Figure 9C:
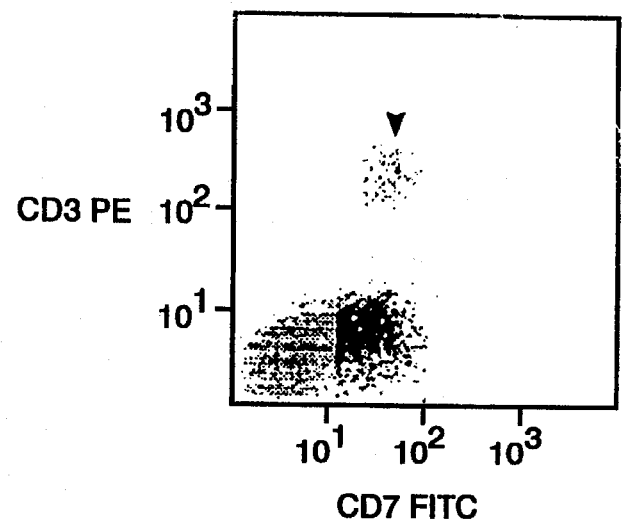
Figure 9D:
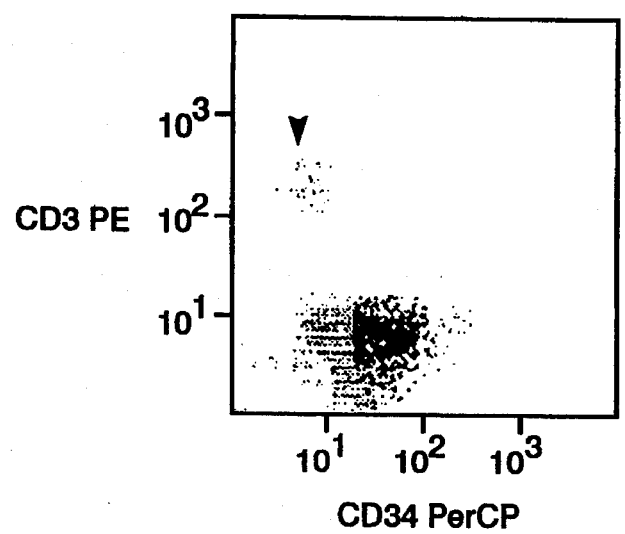

In FIGS. 8A–8D, the bone marrow of the same fetus was stained with anti-Leu 8 PE, CD2 FITC and CD34 PerCp with identical gates as used in FIG. 7. The CD34$^+$, CD2$^+$ (15% depicted black) showed identical light scattering properties (FIG. 8A) as the CD34$^+$, CD7$^+$ population (FIG. 7) all the CD34$^+$, CD2$^+$ coexpressed the Leu 8 antigen (FIGS. 8B and 8C); however, virtually no CD2$^+$ cells expressed the CD34 antigen brightly and the Leu 8 antigen dimly. In addition, fewer bright Leu 8$^+$ cells expressed the CD2 antigen as is indicated with an arrow in FIG. 9B. Taken together, these observations suggest that two distinct precursor populations are present in the fetal marrow—a most immature CD34$^{+++}$, CD7$^+$, CD2$^-$, Leu 8$^{++}$ lymphoid population, and a more mature CD34$^+$, CD7$^+$, CD2$^+$, Leu 8$^{+++}$ T lymphocyte population. This second population being the earliest T lymphocyte precursor.

The CD5 expression on CD34 cells was similar to that of CD2 with slightly fewer cells coexpressing the CD34 and CD5 antigen (1.2%). The CD1, CD3, CD4, CD8 antigens could not be detected on fetal CD34$^+$ T cell precursors (illustrated in FIG. 9 for the CD3 antigen). Note that only a few CD3$^+$, CD7$^+$, CD34$^-$ cells (mature T-cells) are present in the fetal marrow (arrows). The antigenic profile of the CD34$^+$ bone marrow T cell precursor was schematically represented in FIG. 6. The presence of the CD34 and Leu 8 antigen is illustrated in FIG. 6A, the CD4, CD5, CD7, CD8, CD10 and CD38 antigens in FIG. 6B and the CD2, CD44, CD45, CD45RA and CD49$d$ antigens in FIG. 6C.

Taking these data together, the optimal combination of antigens to describe T cell differentiation is CD34, Leu 8, CD3 and CD34, CD1 and CD3. Leu 8 and CD1 antigens show a reciprocal expression during T cell differentiation with up-regulation of CD1 and down regulation of Leu 8 in early T cell differentiation, and down regulation of CD1 and up-regulation of Leu 8 during late T cell differentiation. See FIG. 6.

From FIG. 7, the synchronous differential expression of these antigens can be used to develop a seven-stage thymocyte differentiation scheme: T I=CD34$^{++}$/Leu 8$^{+++}$/CD1$^-$/CD3$^-$; T II=CD34$^+$/Leu 8$^{++}$/CD1$^+$/CD3$^-$; T III=CD34$^{\pm}$/Leu 8$^{++}$/CD1$^{++}$/CD3$^-$; T IV=CD34$^-$/Leu 8$^{++}$/CD1$^{++}$/CD3$^-$; T IV=CD34$^-$/Leu 8$^{++}$/CD1$^{++}$/CD3$^-$; T V=CD34$^{31}$/Leu 8$^+$/CD1$^{++}$/CD3$^+$; T VI=CD34–/Leu 8$^{++}$/CD1$^+$/CD3$^{++}$; and T VII=CD34$^-$/Leu 8$^{+++}$/CD1$^-$/CD3$^{+++}$. The uniformity observed in human thymi in antigen expression patterns and the consistency in frequency of thymocytes in the defined states implies a tightly regulated developmental sequence. See Table II. The coordinated changes in antigen expression throughout thymocyte development will allow in vitro assessment of the regulatory influences required for these changes as well as means to monitor differentiation.

Bone marrow is generally assumed as the source of the T lymphocyte precursor. Although recent studies suggested that early T lymphocyte precursors (i.e., CD7$^+$/CD3$^-$) are detectable in adult bone marrow, those results are not supported here. A CD34$^+$ cell population which coexpressed CD7, CD5 and CD2 antigens and which lacked surface expression of CD3 was found in adult bone marrow. This population, however, was morphologically heterogeneous and major fractions of these cells expressed CD10, CD13, CD33 and CD71 antigens which is consistent with a commitment of these cells to non-T lymphold lineages.

In contrast to adult bone marrow, T lymphocyte precursors were readily found in fetal bone marrow. These precursors expressed CD5, CD2, CD7, CD38 and Leu 8 antigens but lacked surface CD3, CD13, CD19, CD33 and CD71. This population was most easily observed in fetal marrows of gestational age of less than 20 weeks. The antigenic profile of these cells is: CD2$^+$/CD5$^+$/CD7$^+$/CD34$^+$/Leu 8$^{+++}$. The CD7 antigen was expressed on CD34$^{+++}$/Leu 8$^+$ cells, whereas only a small portion of the cells expressed CD2 or CD5. This suggests that CD7 is expressed earlier in T lymphocyte differentiation which, in turn, indicates that the CD7$^+$/CD34$^{+++}$/Leu 8$^+$ contains the earliest T lymphocyte precursor.

Accordingly, in bone marrow, a preferred combination of antibodies for the isolation and identification of a population containing the earliest T lymphocyte precursor is anti-CD34, anti-CD7 and anti-Leu 8. Another combination is anti-CD34, anti-Leu 8 with anti-CD7 being replaced by or used in conjunction with anti-CD5 and/or anti-CD2. In the thymus, a preferred antibody for isolation and identification of the earliest T lymphocyte is anti-CD34; however, a more preferred combination antibodies comprises anti-CD34 and anti-Leu 8 and one or more of anti-CD7, anti-CD2 and anti-CD5. A preferred combination of antibodies for the staging of T lymphocyte differentiation in the thymus is anti-CD34, anti-Leu 8, anti-CD1 and anti-CD3.

Genetic manipulation of any of the above-described T lymphocyte precursor subsets, stage or stages can be carried out by any of the methods described in U.S. Ser. No. 517,101.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

We claim:

1. A substantially pure population of T lymphocyte precursor cells said cells being characterized as CD34$^+$, CD7$^+$ and Leu 8$^+$.

* * * * *